(12) United States Patent
Yasueda et al.

(10) Patent No.: US 7,163,810 B2
(45) Date of Patent: Jan. 16, 2007

(54) METHOD FOR PRODUCING TARGET SUBSTANCE

(75) Inventors: Hisashi Yasueda, Kawasaki (JP); Ryo Takeshita, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 11 days.

(21) Appl. No.: 10/234,329

(22) Filed: Sep. 5, 2002

(65) Prior Publication Data

US 2003/0119155 A1    Jun. 26, 2003

(30) Foreign Application Priority Data

Sep. 6, 2001    (JP) ............................. 2001-270902

(51) Int. Cl.
C12Q 1/02     (2006.01)
C12Q 1/00     (2006.01)
G01N 33/53    (2006.01)
C12P 13/04    (2006.01)
C12P 13/08    (2006.01)

(52) U.S. Cl. ................ 435/106; 424/184.1; 424/185.1; 424/190.1; 424/192.1; 424/234.1; 424/278.1; 435/4; 435/7.2; 435/7.32; 435/29; 435/106; 435/115; 435/243; 435/252.1; 435/252.3; 435/440; 436/86; 436/89; 562/561; 562/562

(58) Field of Classification Search ............. 424/184.1, 424/185.1, 190.1, 192.1, 234.1, 478.1; 435/4, 435/7.2, 7.32, 29, 106, 115, 243, 252.1, 252.3, 435/464; 436/86, 89; 562/562
See application file for complete search history.

(56) References Cited

U.S. PATENT DOCUMENTS 6,083,728 A * 7/2000 Schendel et al. ........... 435/110
6,110,713 A * 8/2000 Hanson et al. .............. 435/110

FOREIGN PATENT DOCUMENTS

EP    0 984 066        3/2000
EP    0 984 066    *   8/2000

OTHER PUBLICATIONS

Lee et al. 1996. Biotechnology and Bioengineering. vol. 49: 639-653.*

(Continued)

Primary Examiner—Lynette R. F. Smith
Assistant Examiner—J. Hines
(74) Attorney, Agent, or Firm—Oblon, Spivak, McClelland, Maier & Neustadt, P.C.

(57) ABSTRACT

In a method for producing a target substance by using a microorganism comprising culturing a microorganism having an ability to produce the target substance in a medium to produce and accumulate the target substance in the medium or cells of the microorganism and collecting the target substance from the medium or the cells of the microorganism, there are used, as the microorganism, a microorganism to which a methanol dehydrogenase gene is introduced, of which activities of hexulose phosphate synthase and phosphohexuloisomerase are enhanced and which is modified so that an ability to utilize methanol should be imparted or enhanced, and there is used a medium containing methanol as a carbon source.

18 Claims, 1 Drawing Sheet

OTHER PUBLICATIONS

Yasueda et al. 1999. J. of Bacteriology. vol. 181(23): 7154-7160.*

H. Yasueda, et al., Journal of Bacteriology, vol. 181, No. 23, pp. 7154-7160, "*Bacillus Subtilis yckG* and *yckF* Encode Two Key Enzymes of the Ribulose Monophosphate Pathway Used by Methylotrophs, and *yckH* is Required for Their Expression", Dec. 1999.

General Meeting of the Society for Bioscience and Bioengineering, p. 9, Aug. 3-5, 200 (with English translation).

G.E. de Vries, et al., Journal of Bacteriology, vol. 174, No. 16, pp. 5346-5353, "Cloning, Expression, and Sequence Analysis of the *Bacillus Methanolicus* C1 Methanol Dehydrogenase Gene", Aug. 1992 (with abstract Accession No. M65004, 2 pages).

N. Arfman, et al., Eur. J. Biochem., vol. 244, pp. 426-433, "Properties of an NAD(H)-Containing Methanol Dehydrogenase and its Activator Protein From *Bacillus Methanolicus*", 1997.

H. Yuirmoto, et al., FEMS Microbiology Letters 214, pp. 189-193, "The Ribulose Monophosphate Pathway Operon Encoding Formaldehyde Fixation in a Thermotolerant Methylotroph, *Bacillus Brevis* S1", 2002.

M. Schallmey, et al., "Developments in the Use of *Bacillus* Species for Industrial Production", Can. J. Microbiol., vol. 50, 2004, pp. 1-17.

* cited by examiner

METHOD FOR PRODUCING TARGET SUBSTANCE

BACKGROUND OF THE INVENTION

1. Field of the Invention

The present invention relates to the microbial fermentation industry, more precisely, a technique of imparting an ability to utilize methanol to a microorganism not originally having such an ability or enhancing such an ability of a microorganism having such an ability at a low level and a method for producing a target substance by utilizing methanol with use of a microorganism obtained by such a technique as mentioned above.

Substances produced according to the present invention include L-amino acids, nucleic acids, antibiotics, vitamins, growth factors, physiologically active substances and so forth, which have conventionally been produced by using microorganisms.

2. Description of the Related Art

To date, most of fermentation raw materials utilized in production of useful substances by microbial fermentation are sugars derived from agricultural products. However, since prices of sugars derived from agricultural products are considered to be on an upward trend in future, an inexpensive material of good quality is desired as an alternative fermentation raw material.

Methanol is easily dissolved in water and inexpensive, and it can be obtained at a high purity. Moreover, it can be comparatively easily produced from methane, which is a main component of natural gas. Therefore it is attractive as a raw material for substance production. If methanol is used as a raw material for microbial fermentation, not only the cost of the main raw material can be reduced, but also purification of products from fermentation solutions and waste solution disposal process can be simplified. Thus, the total production cost can be reduced.

As methods for producing substances, especially amino acids, from methanol as a raw material by utilizing microorganisms, there have been already known a method of utilizing a microorganism of the genus *Achromobacter* or *Pseudomonas* (Japanese Patent Publication (Kokoku) No. 45-25273), a method of utilizing a microorganism of the genus *Protaminobacter* or *Methanomonas* (Japanese Patent Laid-open Publication (Kokai) No. 50-25790), a method of utilizing a microorganism of the genus *Methylobacillus* (Japanese Patent Laid-open Publication No. 4-91793), a method of utilizing a methylotrophic bacterium belonging to the genus *Bacillus* (Japanese Patent Laid-open Publication No. 3-505284, U.S. Pat. No. 6,083,728) and so forth. However, all the bacterial strains have not acquired high productivity of amino acids acceptable as bacteria for practical use.

Meanwhile, methods of utilizing microorganisms of the genus *Brevibacterium, Corynebacterium, Bacillus* or *Escherichia* constitute the mainstream of methods for producing amino acids from glucose ("Amino Acid Fermentation", Ed. by H. Aida et al., Gakkai Shuppan Center). These amino acid producing bacteria are precious bacterial strains bred by introducing various mutations in order to obtain the maximum productivity of amino acids during the long history from the discovery thereof to the breeding of practically useful strains. However, these industrially used strains are microorganisms that cannot utilize methanol.

SUMMARY OF THE INVENTION

An object of the present invention is to provide a novel microorganism having an ability to produce a fermentation product such as an amino acid from methanol as a fermentation raw material by imparting an ability to utilize methanol to a microorganism that is originally can utilize a sugar, but cannot utilize methanol, or enhancing such an ability of a microorganism having the ability at a low level, and a method for producing a target substance from methanol by using such a microorganism.

The inventors of the present invention assiduously studied in order to achieve the aforementioned objects. As a result, they found that, by introducing a methanol dehydrogenase gene into a microorganism and enhancing activities of hexulose phosphate synthase and phosphohexuloisomerase of the microorganism, an ability to utilize methanol can be imparted to the microorganism, or the ability of the microorganism can be enhanced, and thus accomplished the present invention.

That is, the present invention provides the followings.

(1) A method for producing a target substance by using a microorganism comprising culturing a microorganism having an ability to produce the target substance in a medium to produce and accumulate the target substance in the medium or cells of the microorganism and collecting the target substance from the medium or the cells of the microorganism, wherein the microorganism is a microorganism to which a methanol dehydrogenase gene is introduced and which is modified so that activities of hexulose phosphate synthase and phosphohexuloisomerase shoud be enhanced and an ability to utilize methanol should be imparted or enhanced, and the medium contains methanol as a carbon source.

(2) The method according to (1), wherein the target substance is an L-amino acid.

(3) The method according to (2), wherein the L-amino acid is L-lysine.

(4) The method according to (3), wherein the microorganism is a bacterium belonging to the genus *Bacillus*.

(5) A microorganism to which a methanol dehydrogenase gene is introduced, wherein the microorganism is modified so that hexulose phosphate synthase and phosphohexuloisomerase should be enhanced and an ability to utilize methanol should be imparted or enhanced.

(6) The microorganism according to (5), which is a Gram positive bacterium.

(7) The microorganism according to (6), which is a bacterium belonging to the genus *Bacillus*.

(8) The microorganism according to (7), which is *Bacillus subtilis*.

According to the present invention, an ability to utilize methanol can be imparted to a microorganism not originally having such an ability or such an ability of a microorganism having the ability at a low level can be enhanced, and thus there can be provided a microorganism that can utilize inexpensive methanol as a carbon source or energy source utilized by the microorganism. Further, by utilizing the obtained microorganism, various fermentation products can be produced from methanol in a medium added with methanol.

PREFERRED EMBODIMENTS OF THE INVENTION

Figure 1:
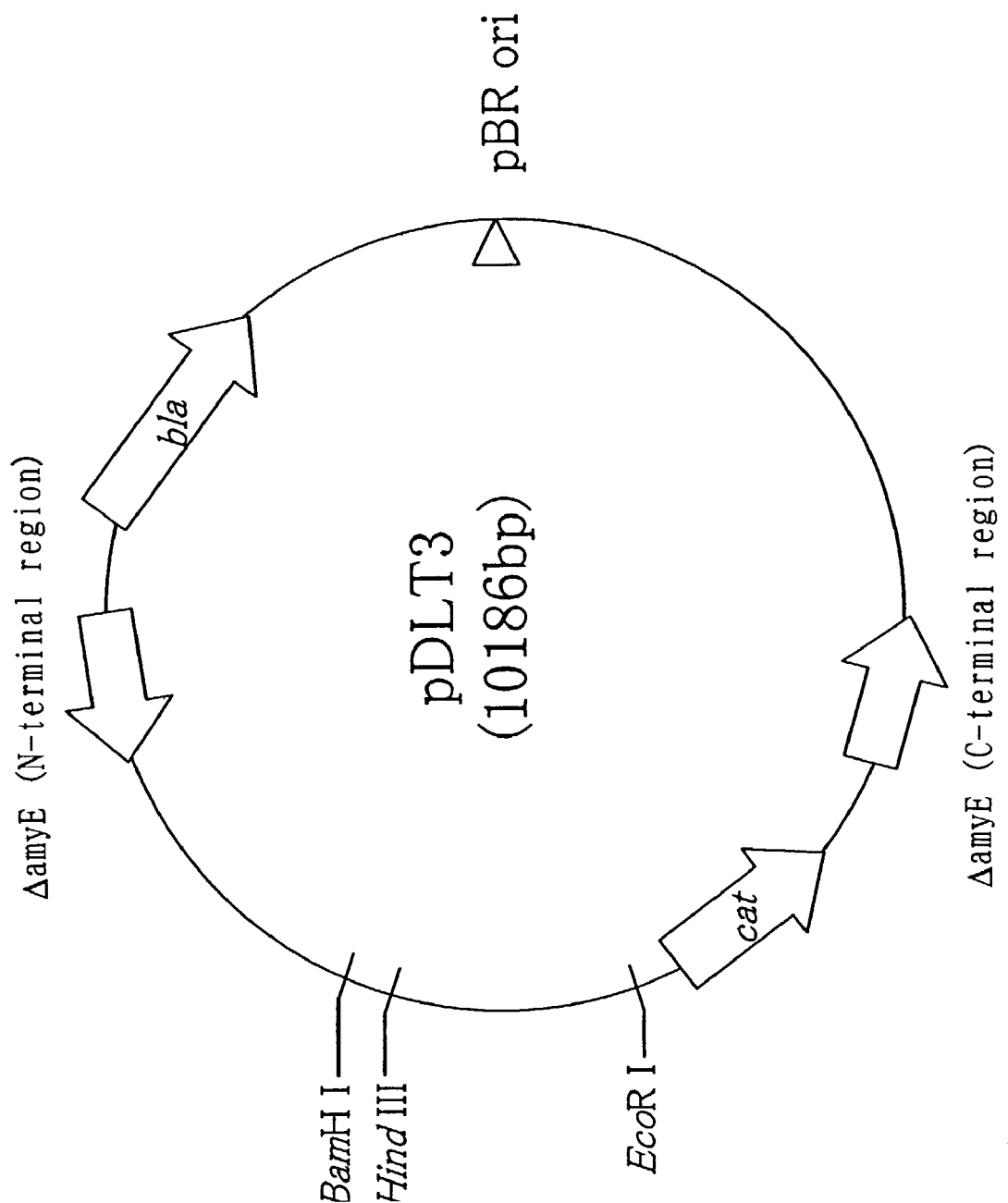
FIG. 1 shows the structure of the plasmid pDLT3 for introducing a gene into chromosome. The symbol "cat" represents a chloramphenicol resistance gene, "bla" represents an ampicillin resistance gene and "pBR ori" represents a replication origin of pBR322.

Hereafter, the present invention will be explained in detail.

The microorganism of the present invention is a microorganism to which a methanol dehydrogenase gene is introduced and which is modified so that activities of hexulose phosphate synthase and phosphohexuloisomerase shoud be enhanced and an ability to utilize methanol should be imparted or enhanced. Although a parent strain used for construction of the microorganism of the present invention may be a microorganism originally having a weak ability to utilize methanol, it is preferably a microorganism that originally can utilize a sugar, but cannot utilize methanol.

A microorganism that can utilize methanol has a methanol oxidase (e.g., methanol dehydrogenase) and it dissimilates and assimilates formaldehyde produced by oxidation of methanol through precise metabolic regulation. This is because formaldehyde is strongly toxic for organisms and therefore cells must rapidly utilize it as a carbon source or energy source or dispose it by detoxification. Therefore, if there is contemplated imparting an ability to utilize methanol to a microorganism that cannot utilize methanol, it is of course indispensable to introduce a methanol oxidase. However, there are scarcely specific measures for proper disposal of formaldehyde produced due to expression of the methanol oxidase activity, and therefore it has been considered that it should be impossible to impart an ability to utilize methanol to an arbitrary microorganism.

However, the inventors of the present invention found that the ability to utilize methanol could be imparted even to a microorganism that originally cannot utilize methanol, if an enzyme having methanol oxidation ability was made to exist in cells of the microorganism and further hexulose phosphate synthase activity and phosphohexuloisomerase activity of the microorganism were enhanced.

The microorganism used for the present invention is not particularly limited so long as the aforementioned properties characteristic to the microorganism of the present invention can be imparted, and there can be specifically mentioned bacteria belonging to the genus *Bacillus* such as *Bacillus subtilis*, *Escherichia* bacteria such as *Escherichia coli*, coryneform bacteria such as and *Brevibacterium lactofermentum* (*Corynebacterium glutamicum*), *Serratia* bacteria such as *Serratia marcescens* and so forth. Among these, Gram positive bacteria, especially bacteria belonging to the genus *Bacillus*, are preferred.

Specifically, there can be mentioned *Escherichia coli* VKPM B-3996 (RIA 1867, refer to U.S. Pat. No. 5,175,107), *Corynebacterium acetoacidophilum* AJ12318 (FERM BP-1172, refer to U.S. Pat. No. 5,188,949) etc. for L-threonine as the fermentation product; *Bacillus subtills* AJ11779 (FERM P-18453), *Bacillus subtilis* AJ13291 (FERM P-6722, refer to Japanese Patent Laid-open Publication No. 59-63193), *Escherichia coli* AJ11442 (NRRL B-12185, FERM BP-1543, refer to U.S. Pat. No. 4,346,170), *Escherichia coli* W3110 (tyrA) (this strain can be obtained by eliminating plasmid pHATerm from *Escherichia coli* W3110 (tyrA)/pHATerm (FERM BP-3653), refer to International Patent Publication WO95/16042), *Brevibacterium lactofermentum* AJ12435 (FERM BP-2294, U.S. Pat. No. 5,304, 476), *Brevibacterium lactofermentum* AJ3990 (ATCC 31269, refer to U.S. Pat. No. 4,066,501) etc. for L-lysine as the same; *Escherichia coli* AJ12624 (FERM BP-3853, refer to French Patent Laid-open Publication No. 2,680,178), *Brevibacterium lactofermentum* AJ12821 (FERM BP-4172, Japanese Patent Laid-open Publication No. 5-26811, French Patent Laid-open Publication No. 2,701,489), *Brevibacterium lactofermentum* AJ12475 (FERM BP-2922, refer to U.S. Pat. No. 5,272,067), *Brevibacterium lactofermentum* AJ13029 (FERM BP-5189, refer to International Patent Publication JP95/01586) etc. for L-glutamic acid as the same; *Escherichia coli* AJ11478 (FERM P-5274, refer to Japanese Patent Publication No. 62-34397), *Brevibacterium lactofermentum* AJ3718 (FERM P-2516, refer to U.S. Pat. No. 3,970,519) etc. for L-leucine as the same; *Escherichia coli* KX141 (VKPM B-4781, refer to European Patent Laid-open Publication No. 519,113), *Brevibacterium flavum* AJ12149 (FERM BP-759, refer to U.S. Pat. No. 4,656,135) etc. for L-isoleucine as the same; *Escherichia coli* VL1970 (VKPM B-4411, refer to European Patent Laid-open Publication No. 519,113), *Brevibacterium lactofermentum* AJ12341 (FERM BP-1763, refer to U.S. Pat. No. 5,188,948) etc. for L-valine as the same; *Bacillus subtilis* AJ12000 (FERM P-6895, refer to Japanese Patent Laid-open Publication No. 59-143596), *Escherichia coli* AJ12604 (FERM BP-3579, refer to Japanese Patent Laid-open Publication No. 5-236947, European Patent Laid-open Publication No. 488,424), *Brevibacterium lactofermentum* AJ12637 (FERM BP-4160, refer to French Patent Laid-open Publication No. 2,686,898) etc. for L-phenylalanine as the same; *Bacillus subtilis* AJ11488 (FERM P-5290, refer to Japanese Patent No. 1426798), *Escherichia coli* KB862 (DSM7196, refer to European Patent No. 662,143) etc. for L-tryptophan as the same and so forth.

As a result of assiduous studies, the inventors of the present invention conceived of obtaining sufficient exertion of methanol dehydrogenase activity in cells and enhancement of a function for assimilating formaldehyde produced by the enzymatic reaction as fundamental conditions for imparting the ability to utilize methanol. The inventors of the present invention further conceived that enhancement of enzymatic activities of hexulose phosphate synthase (HPS) and phosphohexuloisomerase (PHI), which are key enzymes of the ribulose monophosphate pathway, would be effective for effective assimilation of formaldehyde. Thus, they found that the ability to utilize methanol could be imparted to a microorganism that originally could not utilize methanol by introducing a methanol dehydrogenase gene into the microorganism and enhancing activities of HPS and PHI.

The methanol dehydrogenase (MDH) used for the present invention is an enzyme having an enzymatic activity that can oxidize methanol to convert it into formaldehyde. For example, PQQ (pyrroloquinolinequinone) dependent type MDH, which is mainly seen in Gram negative microorganisms, can be mentioned as MDH that can be used for the present invention. Specifically, MDH of *Methylobacterium extorquens* AM1 strain (Biochim. Biophys. Acta, 1119: 97–106 (1992)) etc. can be mentioned. Further, NAD (nicotinamide adenine dinucleotide) dependent type MDH seen in Gram positive microorganisms, specifically, MDH of *Bacillus methanoliocus* (J. Bacteriol., 174:5346–5353 (1992)), alcohol dehydrogenase (ADH) derived from *Bacillus stearothermophilus* DSM 2334 strain (Biochem. J., 252:661–666) etc. can be mentioned. Furthermore, ADH in bovine liver (Biochem. J., 100:34–46 (1966)) and human liver (Arch. Toxicol., 72:604–607 (1998)) can also be mentioned. Further, a mutant type alcohol dehydrogenase that significantly acts also on methanol can also be newly created by introducing a mutation into a gene of alcohol dehydrogenase that originally does not act on methanol to modify its substrate specificity, and used. However, as MDH that can be suitably used for the present invention, MDH derived form, for example, *Bacillus brevis* NCIMB No. 12524, which is a methanol-assimilating bacterium belonging to the genus *Bacillus*, can be specifically mentioned.

A gene coding for MDH (mdh) can be obtained from a microorganism that produces MDH in the same manner as that used in ordinary gene cloning method. For example, an MDH gene can be obtained by PCR (polymerase chain reaction) using chromosomal DNA of *Bacillus brevis* S1 strain (NCIMB 12524) as a template and oligonucleotides having the nucleotide sequences shown as SEQ ID NOS: 1 and 2 as primers. Methods for preparation of genomic DNA library used for gene cloning, hybridization, PCR, preparation of plasmid DNA, digestion and ligation of DNA, transformation etc. are described in Sambrook, J., Fritsch, E. F., Maniatis, T., Molecular Cloning, Cold Spring Harbor Laboratory Press, 1.21 (1989). In addition, whether a MDH gene is functioning in a microorganism to which the gene is introduced can be confirmed by measuring MDH activity of lysate of the microorganism. The MDH activity can be measured by, for example, a method of measuring reduction of $NAD^{30}$ (nicotinamide adenine dinucleotide) accompanying the oxidation of methanol into formaldehyde through measurement of absorbance for a light at a wavelength of 340 nm.

As a specific example of the mdh gene used for the present invention, mdh gene of *Bacillus brevis* S1 strain can be mentioned. The mdh gene of *Bacillus methanolicus* C1 strain (NCIMB 13114, Eur. J. Biochem., 244:426–433 (1997)) has been registerd in GenBank under Accession M65004 (entry name of BACMDH).

In addition, there has been reported existence of factors for activating activity of methanol dehydrogenase (Amd: Activator of methanol dehydrogenase). For example, there are the activator for methanol dehydrogenase of *Bacillus methanolicus* C1 strain (Eur. J. Biochem., 244:426–433 (1997)) and the YqkG gene product of *Bacillus subtilis* 168 strain (Japanese Patent Laid-open Publication No. 2000-69976). Use of these is effective means for enhancing activity of MDH. By introducing DNA coding for any of these MDH activators (amd gene) into a microorganism containing an MDH gene, MDH activity in cells of the microorganism can be enhanced. A gene coding for Amd (amd) such as the YqkG gene can be obtained from chromosomal DNA of *Bacillus subtilis* such as the *Bacillus subtilis* 168 strain by PCR using the chromosomal DNA as a template and primers having the nucleotide sequences shown as SEQ ID NOS: 10 and 11 in Sequence Listing.

As a specific example of the yqkG gene used for the present invention, the YqkG gene of *Bacillus subtilis* 168 strain can be mentioned. The nucleotide sequence and the amino acid sequence encoded by this gene are shown as SEQ ID NOS: 14 and 15.

Methods for enhancing the activities of HPS and PHI of a microorganism will be explained hereafter.

In order to amplify HPS or PHI activity in a target microorganism, a recombinant DNA can be prepared by ligating a gene coding for HPS (hps) or PHI (phi) with a vector functioning in the target microorganism, preferably a multi-copy type vector, and introduced into the target microorganism to transform it. The copy number of the hps gene or phi gene in the cell of the transformant strain is thereby increased, and as a result, either of the enzymatic activities is amplified.

The hps or phi gene can be obtained from a microorganism that produces HPS or PHI in the same manner as used in ordinary gene cloning method, like the MDH gene.

As the microorganism that produces HPS, there are known *Methylomonas capsulatus* (J. R. Quayle, Methods in Enzymology, 188, p. 314, 1990), *Methylomonas* M15 strain (Methods in Enzymology, 188, p. 319, 1990), *Methylomonas aminofaciens* 77a strain (Biochim. Biophys. Acta., 523, p. 236, 1978), *Mycobacterium gastri* MB19 (Methods in Enzymology, 188, p. 393, 1990), *Acetobacter methanolicus* MB58 (Methods in Enzymology, 188, p. 401, 1990) etc. Further, as the microorganism that produces PHI, there are known *Methylomonas aminofaciens* 77a strain (Agric. Biol. Chem., 41 (7), p1133, 1977), *Mycobacterium gastri* (Japanese Patent Laid-open Publication No. 11-127869), which is a Gram positive facultative methanol-assimilating bacterium, etc. Further, both of the hps and phi genes have been reported for *Bacillus subtilis* (J. Bacteriol., 181:7154–7160 (1999)). Furthermore, it has been reported that, in the *Bacillus brevis* S1 strain, which is a methanol-assimilating bacterium belonging to the genus *Bacillus*, the hps gene and phi gene exist in tandem on chromosomal DNA (Annual Meeting of the Society for Fermentation and Bioengineering Japan, Lecture Abstracts, p. 113 (2000)). A DNA fragment containing the hps and phi genes can be obtained by PCR using chromosomal DNA of the strain as a template and oligonucleotides having the nucleotide sequences shown as SEQ ID NOS: 12 and 13 as primers.

As specific examples of the hps gene and phi gene used for the present invention, the hps gene and phi gene of *Bacillus subtilis* 168 strain can be mentioned. The nucleotide sequence of DNA fragment comprising the hps and phi genes of *Bacillus brevis* S1 strain is shown as SEQ ID NO: 16. The amino acid sequences encoded by the genes are shown as SEQ ID NOS: 17 and 18.

The *Bacillus methanolicus* C1 strain (NCIMB 13114) and *Bacillus brevis* S1 strain (NCIMB 12524) can be obtained from National Collections of Industrial and Marine Bacteria, Address: NCIMB Lts., Torry Research Station135, Abbey Road, Aberdeen AB9 8DG, United Kingdom).

The HPS activity can be measured by the method described in Methods in Enzymology, 188, 397–401 (1990). Further, the PHI activity can be measured by the method described in Journal of Bacteriology, 181, p. 7154–7160 (1999).

Amplification of the HPS or PHI activity can also be achieved by introducing multiple copies of the hps gene or phi gene into chromosomal DNA of a target microorganism. In order to introduce multiple copies of the hps gene or phi gene into chromosomal DNA of a target microorganism, homologous recombination is carried out by using a sequence whose multiple copies exist in the chromosomal DNA as a target. As sequences whose multiple copies exist in chromosomal DNA, repetitive DNA or inverted repeat existing at the end of a transposable element can be used. Further, as disclosed in Japanese Patent Laid-open Publication No. 2-109985, it is also possible to incorporate the hps gene or phi gene into transposon, and allow it to be transferred to introduce multiple copies of the genes into chromosomal DNA. According to any of these methods, the HPS or PHI activity is amplified as a result of increase of copy numbers of the hps gene or phi gene in the transformant strain.

The amplification of HPS or PHI activity can also be attained by, besides being based on the aforementioned gene amplification, replacing an expression regulatory sequence such as a promoter of the hps gene or phi gene with a stronger one (refer to Japanese Patent Laid-open Publication No. 1-215280). For example, lac promoter, trp promoter, trc promoter, tac promoter, $P_R$ promoter and $P_L$ promoter of lambda phage, tet promoter, amyE promoter, veg promoter and so forth are known as strong promoters. Substitution of these promoters enhances expression of the hps gene or phi gene, and hence the HPS or PHI activity is amplified. The enhancement of expression regulatory sequence may be combined with increase of copy number of HPS or PHI.

The mdh, hps, phi and amd genes used for the present invention are not limited to wild-type genes, and they may be a mutant or artificially modified gene coding for a gene product including substitution, deletion, insertion, addition or inversion of one or several amino acids at one or more sites, so long as the function of the encoded MDH, HPS, PHI or Amd protein is not degraded. Although the number of "several" amino acids referred to herein differs depending on position or type of amino acid residues in a three-dimensional structure of a protein, it may be specifically 2 to 20, preferably 2 to 10, more preferably 2 to 5.

As DNA coding for a protein substantially identical to the aforementioned Amd protein, there can be mentioned DNA that is hybridizable with a nucleotide sequence comprising the sequence of the nucleotide numbers 1 to 555 in SEQ ID NO: 16 or a probe that can be produced from the nucleotide sequence under stringent conditions and codes for a protein having an activity similar to that of Amd.

Further, as DNA coding for a protein substantially identical to the HPS protein, there can be mentioned DNA that is hybridizable with a nucleotide sequence comprising the sequence of the nucleotide numbers 508 to 1140 in SEQ ID NO: 16 or a probe that can be produced from the nucleotide sequence under stringent conditions and codes for a protein having an activity similar to that of HPS.

Further, as DNA coding for a protein substantially identical to the PHI protein, there can be mentioned DNA that is hybridizable with a nucleotide sequence comprising the sequence of the nucleotide numbers 1149 to 1700 in SEQ ID NO: 16 or a probe that can be produced from the nucleotide sequence under stringent conditions and codes for a protein having an activity similar to that of PHI.

Further, as DNA coding for a protein substantially identical to the MDH protein, there can be mentioned DNA that is hybridizable with a nucleotide sequence registered in GenBank under Accession M65004 (entry name of BAC-MDH) or a probe that can be produced from the nucleotide sequence under stringent conditions and codes for a protein having an activity similar to that of MDH.

The aforementioned "stringent conditions" is a condition under which a so-called specific hybrid is formed, and a non-specific hybrid is not formed. It is difficult to clearly express this condition by using any numerical value. However, for example, the stringent conditions is exemplified by a condition under which DNA's having high homology, for example, DNA's having homology of 50% or more are hybridized with each other, but DNA's having homology lower than the above are not hybridized with each other. Alternatively, the stringent conditions is exemplified by a condition under which DNA's are hybridized with each other at a salt concentration corresponding to an ordinary condition of washing in Southern hybridization, i.e., 1×SSC, 0.1% SDS, preferably 0.1×SSC, 0.1% SDS, at 60° C.

To introduce the various genes that can be obtained as described above into a microorganism, for instance, employable are a method of treating recipient cells with calcium chloride so as to increase the permeability for DNA, which has been reported for *Escherichia coli* K-12 (Mandel, M. and Higa, A., J. Mol. Biol., 53, 159 (1970)), and a method of preparing competent cells from cells which are at the growth phase, followed by introducing the DNA thereinto, which has been reported for *Bacillus subtilis* (Duncan, C. H., Wilson, G. A. and Young, F. E., Gene, 1, 153 (1977)). In addition to these, also employable is a method of making DNA-recipient cells into protoplasts or spheroplasts, which can easily take up a recombinant DNA, followed by introducing a recombinant DNA into the cells, which is known to be applicable to *Bacillus subtilis*, actinomycetes and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)). Furthermore, electroporation method can be used (Canadian Journal of Microbiology, 43, 197 (1997)). Any of these methods can be suitably selected depending on the cells used as a recipient.

In the microorganism used for the present invention, according to type of the target substance, activity of an enzyme involved in the biosynthesis of the target substance may be enhanced. Further, activity of an enzyme disadvantageous for the production of the target substance may be reduced or eliminated.

When the mdh, hps, phi genes and amd gene as required are introduced into a microorganism, order of the introduction of the genes is not particularly limited. Further, the microorganism of the present invention can be obtained either by introducing these genes into a microorganism having an ability to produce a target substance, or by imparting an ability to produce a target substance to a microorganism introduced with these genes.

A target substance can be produced with use of methanol by culturing the microorganism of the present invention obtained as described above in a medium to produce and accumulate the target substance in the medium or cells of the microorganism and collecting the target substance from the medium or the cells of the microorganism.

Target substances to which the method of the present invention is applicable include, for example, substances produced by metabolism of methanol and substances produced by utilizing energy generated by metabolism of methanol. Specifically, there can be mentioned, for example, amino acids such as glutamic acid, lysine, threonine, phenylalanine and tryptophan, vitamins such as vitamin C, macromolecular substances such as various kinds of enzymes and so forth.

The term "ability to produce a target substance" used in the present invention means an ability of the microorganism of the present invention to produce and accumulate the target substance in a medium or cells of the microorganism in such an amount that the substance can be collected therefrom, when the microorganism is cultured in the medium under suitable conditions.

Although the medium and culture conditions used for the culture in the method of the present invention may be suitably selected depending on the type of the microorganism used, there can be used ordinary media containing a nitrogen source, inorganic ions, and other organic trace amount nutrients as required.

As a carbon source, methanol is used. Together with methanol, there can be used saccharides such as glucose, lactose, galactose, fructose and starch hydrolysate, alcohols such as glycerol and sorbitol, or organic acids such as fumaric acid, citric acid and succinic acid.

As the nitrogen source, there can be used inorganic ammonium salts such as ammonium sulfate, ammonium chloride and ammonium phosphate, organic nitrogen such as soybean protein hydrolysate, ammonia gas, aqueous ammonia and so forth.

As inorganic ions or a source thereof, potassium phosphate, magnesium sulfate, iron ion, manganese ion and so forth are added in small amounts. As organic trace amount nutrients, it is desirable to add required substances such as L-homoserine and vitamin $B_1$, yeast extract and so forth in appropriate amounts as required.

The culture is preferably carried out under conditions suitable for the microorganism used. Usually, the culture is preferably carried out under an aerobic condition for 16–72 hours. Culture temperature is preferably controlled to be 20° C. to 45° C., and pH is preferably controlled to be 5 to 8.5 during the culture. Inorganic or organic, acidic or alkaline substances as well as ammonia gas and so forth can be used for pH adjustment. If a thermophilic bacterium is used as a host, it can be cultured at a culture temperature of 42° C. to 60° C.

For collection of the metabolic product from the medium after completion of the culture, any special method is not required for the present invention. That is, it can be carried out by a combination of well-known techniques such as methods utilizing ion exchange resins, precipitation and other techniques. In addition, when methanol is used as the carbon source, purification of the target substance and waste solution disposal process may be simplified compared with a case of using sugars derived from agricultural products.

EXAMPLES

Hereafter, the present invention will be explained more specifically with reference to the following examples.

Example 1

Cloning of Methanol Dehydrogenase Gene

Chromosomal DNA was prepared in a conventional manner from *Bacillus brevis* S1 strain (NCIMB 12524, obtained from NCIMB), which is a methanol-assimilating high-temperature resistant bacterium belonging to the genus *Bacillus*. Then, an MDH gene was cloned by PCR method using this DNA as a template (refer to Japanese Patent Laid-open Publication No. 2000-69976).

The DNA primers used were MDH-BM-1 (SEQ ID NO: 1) and MDH-BM-2 (SEQ ID NO: 2). These were prepared by referring to the already known nucleotide sequence of the MDH gene of *Bacillus methanolicus* C1 strain (registered at GenBank under Accession M65004, entry name of BAC-MDH). PCR was performed by using LA-Taq (Takara Shuzo) and consisted of a heat treatment at 94° C. for 90 seconds, following reactions at 98° C. for 10 seconds, 55° C. for 30 seconds and 70° C. for 4 minutes repeated for 30 cycles, and further following incubation at 72° C. for 10 minutes. A DNA fragment of the desired size was obtained by these reactions. This DNA fragment was purified and then cloned into a commercially available vector, pCR2.1, to obtain pCP-mdh24-1.

In order to introduce the mdh gene contained in the aforementioned pCP-mdh24-1 into chromosome of *Bacillus subtilis*, the mdh gene was incorporated into a vector for introducing a gene into chromosome, plasmid pDLT3. pDLT3 was prepared in a conventional recombinant DNA technique for introduction of a target gene into amyE site of *Bacillus subtilis* chromosome, and its entire nucleotide sequence is shown as SEQ ID NO: 3.

pDLT3 was prepared as follows (FIG. 1). First, in order to remove the lacZ gene segment from pMUTIN3 (described in Molecular Microbiology, 29 (1), 179–187 (1998)), the plasmid was digested with restriction enzymes Cl aI and Bpu1102I. Then, the digested ends were blunt-ended with Klenow enzyme, and the larger DNA fragment was self-ligated by using T4 ligase. Subsequently, pDLd (described in Molecular Microbiology, 29 (2), 505–513 (1998)) was similarly digested by a restriction enzyme treatment, and a larger DNA fragment (Tth111I-BamHI) was isolated. A Tth111I-Bgl II DNA fragment of the plasmid containing lacI and spac promoters was ligated to the larger DNA fragment to construct pDLT3.

The plasmid pDLT3 was treated with restriction enzymes BamHI and EcoRI in a conventional manner to prepare a larger DNA fragment. Separately, pCR-mdh24-1 was similarly treated with restriction enzymes BamHI and EcoRI in a similar manner to prepare a DNA fragment containing the mdh gene. Both of these DNA fragments were ligated by using T4 ligase to construct a plasmid pDLT-MD11, in which the mdh gene was incorporated between the first half region and the second half region of the amyE gene on pDLT3.

The obtained cyclic plasmids, pDLT-MD11 and pDLT3, were linearized by a treatment with a restriction enzyme Bst1107I, and the *Bacillus subtilis* 168 strain was transformed with each of them in a conventional manner. The transformants were selected as chloramphenicol resistant strains. Since many chloramphenicol resistant strains were obtained for each case, six colonies were selected for each and it was investigated whether only the mdh gene or the vector was introduced into the amyE site on the chromosome as intended. Whether the linearized mdh gene should be introduced through twice of the recombination processes was confirmed by colony PCR. The DNA primers used were N1, N2, N3, C1, C2 and C3 (SEQ ID NOS: 4, 5, 6, 7, 8 and 9, respectively, in that order). As a result of analysis of DNA fragments amplified by PCR, AM101 strain was selected as a strain having a structure in which the mdh gene was incorporated into the intended region. On the other hand, a strain in which the vector region was incorporated was selected as a control strain and designated as DT101 strain.

Then, the MDH activity expressed in the AM101 strain was determined by using the DT101 strain as a control. The both strains were each inoculated into 30 ml of LB medium containing 5 μg/ml of chloramphenicol and cultured at 30° C. for about 16 hours. The culture broth was centrifuged (10,000 g, 10 minutes) to collect the cells as precipitates, and then the cells were suspended in 0.8 ml of suspension buffer (composition: 5 ml of 0.1 M phosphate buffer (pH 7.6), 1 ml of 50 mM magnesium sulfate, 0.1 ml of 0.2 M dithiothreitol, 3.3 ml of 60% sucrose and 0.6 ml of sterilized water per 10 ml) and disrupted by ultrasonication while maintaining the temperature of the suspension at a temperature lower than 4° C. Then, solid matter contained in the suspension was removed by centrifugation (17000 g, 10 minutes) of the suspension at 4° C. to prepare a cell extract.

The MDH enzymatic activity was measured as follows. First, 0.9 ml of reaction buffer (10 ml of 0.1 M glycine/potassium hydroxide (pH 9.5), 2 ml of 50 mM magnesium sulfate, 0.1 ml of 0.2 M dithiothreitol, 0.5 ml of 40 mM NAD, 7.4 ml of sterilized water per 20 ml) was put into a 1.5-ml volume quartz cuvette, and the cuvette was mounted on a spectrometer. In the spectrometer, the temperature of the reaction mixture was controlled by incubation at 47° C. for 3 minutes. Then, 50 μl of the cell extract prepared by the procedure described was added to the reaction mixture and stirred sufficiently. At the same time, there was started measurement of absorbance of the reaction mixture at 340 nm, at which NADH shows the absorption maximum, to investigate absorbance variation under a condition that methanol was absent. Further, after about 60 seconds, 50 μl of methanol was added to the reaction mixture and stirred sufficiently, and increase of absorbance at 340 nm, i.e., generation of NADH, was further observed and recorded. Increase of absorbance at 340 nm due to MDH was not observed when the cell extract of the control strain, DT101 strain, was used. However, when the extract of the AM101 strain was used, there was observed increase of absorbance at 340 nm depending on the addition of methanol, and it was confirmed that MDH should exist in this strain. Thus, it was found that the mdh gene incorporated into the chromosome of *Bacillus subtilis* coded for an MDH enzyme that could exhibit the enzymatic activity. NAD and NADH represent oxidized type and reduced type nicotinamide adenine dinucleotide, respectively.

Example 2

Incorporation of mdh into Chromosome of L-lysine-producing *Bacillus subtilis* Strain The *Bacillus subtilis* AJ11779 strain modified so that it could produce L-lysine is a strain described in Japanese Patent Laid-open Publication No. 58-149689. To this strain, the L-lysine producing ability was imparted by imparting resistance to the growth inhibition by AEC, which is lysine analogue compound and threonine. This strain was deposited at the independent administrative institution, National Institute of Advanced Industrial Science and Technology, International Patent Organism Depositary (Address: postal code 305-5466, Chuo Dai-6, 1-1 Higashi 1-Chome, Tsukuba-shi, Ibaraki-ken, Japan) on Aug. 9, 2001 and given with an accession number of FERM P-18453. Then, the deposition was changed to an international deposition under the provisions of the Budapest Treaty on Aug. 19, 2002 and given with an accession number of FERM BP-8155.

It was planned to incorporate the mdh gene described in Example 1 into the amyE site in the chromosome of the AJ11779 strain. First, the cyclic plasmid pDLT-MD11 was linearized by a treatment with a restriction enzyme Bst1107I and used to transform the AJ11779 strain in a conventional manner. Transformants were selected as chloramphenicol resistant strains.

Since many chloramphenicol resistant strains were obtained, two or more colonies were picked up from them, and a strain in which the mdh gene was introduced into the amyE site on the chromosome was selected in the same manner as in Example 1. The obtained strain was designated as L-217M1 strain.

A cell extract was prepared from this L-217M1 strain and the MDH activity was measured in the same manner as in Example 1. As a result, the MDH activity could be detected.

Example 3

Cloning of Gene Coding for MDH Activator (Amd) Derived from *Bacillus subtilis*

It is known that there are factors for activating enzymatic activity of NAD-dependent type methanol dehydrogenases derived from methanol-assimilating bacteria belonging to the genus *Bacillus*. Japanese Patent Laid-open Publication No. 2000-69976 (OP884) discloses that one of such factors exists in *Bacillus subtilis*. This factor was designated as Amd (Activator of methanol dehydrogenase).

The gene coding for Amd (amd) was cloned from *Bacillus subtilis* in an already known manner. Specifically, the cloning was carried out as follows. The *Bacillus subtilis* 168 strain was cultured in LB medium, and chromosomal DNA was extracted from the obtained cells in a conventional manner (Biochem. Biophys. Acta., 72, 619–629 (1963)). This chromosomal DNA was used as a template in PCR using such oligonucleotides that the target DNA fragment should have EcoRI restriction enzyme sites on the both ends (SEQ ID NOS: 10 and 11) to amplify a gene DNA fragment containing and, which was the target gene. For the amplification, a cycle consisting of a denaturation step at 98° C. for 10 second, annealing step at 55° C. for 30 second and extension step at 72° C. for 2 minutes was repeated for 30 cycles. The enzyme used was Pyrobest DNA polymerase (Takara Shuzo), and it was used according to the manufacture's instruction.

The amplified DNA fragment was purified by phenol/chloroform treatment and ethanol precipitation and then digested with a restriction enzyme EcoRI to prepare an amd fragment having EcoRI sites at the both ends. Separately, pHY300PLK (Takara Shuzo), which is a shuttle vector for *Escherichia coli* and *Bacillus subtilis*, was similarly treated with a restriction enzyme EcoRI. After the phosphate groups at the ends were removed by using an alkaline phosphatase, it was ligated to the aforementioned amd fragment. By using this ligation reaction mixture, competent cells of *E. coli* JM109 strain (Takara Shuzo) were transformed according to the manufacturer's protocol, and several tetracycline resistant colonies were selected.

Plasmid DNA was extracted from these colonies and analyzed for the structure. Then, plasmids containing the amd gene in the same direction as the direction of the tetracycline resistance gene of the vector and in the inverse direction were designated as pHY-A2 and pHY-A1, respectively, and used for the following experiments.

The activity of Amd that enhances the MDH activity was investigated as follows. The *Bacillus subtilis* AM101 strain incorporated with the mdh gene as constructed in Example 1 was transformed in a conventional manner with each of pHY-A1 and pHY-A2 as well as pHY300PLK, which is a vector plasmid. Then, a cell extract was prepared from each transformant as follows.

Each transformant strain was inoculated into 30 ml of LB medium containing 5 μg/ml of chloramphenicol and 10 μg/ml of tetracycline and cultured at 30° C. for about 16 hours. Each culture broth was centrifuged (at 10,000 g for 10 minutes) to collect the cells as precipitates, and then the cells were suspended in 0.8 ml of suspension buffer (5 ml of 0.1 M phosphate buffer (pH 7.6), 1 ml of 50 mM magnesium sulfate, 0.1 ml of 0.2 M dithiothreitol, 3.3 ml of 60% sucrose and 0.6 ml of sterilized water per 10 ml) and disrupted by ultrasonication while maintaining the temperature of the suspension at a temperature of 4° C. to prepare a cell extract.

The enhancement of the MDH enzymatic activity by Amd was measured by the assay described below. In a volume of 0.9 ml of reaction buffer (10 ml of 0.1 M glycine/potassium hydroxide (pH 9.5), 2 ml of 50 mM magnesium sulfate, 0.1 ml of 0.2 M dithiothreitol, 0.5 ml of 40 mM NAD, 7.4 ml of sterilized water per 20 ml) was incubated in a quartz cuvette at 37° C. for 3 minutes. Then, 50 μl of the cell extract prepared as described above was added to the reaction mixture and stirred. At the same time, there was started time course measurement of absorbance of the reaction mixture at 340 nm, at which NADH shows the absorption maximum, and variation of the absorbance at 340 nm, which was not related to addition of methanol, was recorded. Further, about 60 seconds after that, 50 μl of methanol was added to the reaction mixture and stirred, and increase of absorbance at 340 nm, i.e., generation of NADH, at that time was investigated. As a result, compared with the increasing rate of absorbance at 340 nm due to the presence of MDH observed for the case utilizing the cell extract of the strain introduced with pHY300PLK, a substantially equivalent increasing rate of absorbance at 340 nm was observed for the case of using the strain introduced with pHY-A1, and a 5 times higher NADH producing rate was observed for the case of using the strain introduced with pHY-A2. Thus, it was confirmed that Amd encoded by pHY-A2 should surely had the activity for enhancing the MDH activity.

Example 4

Cloning of hps Gene and phi Gene from Methanol-assimilating Bacterium Belonging to the Genus *Bacillus*

Chromosomal DNA was prepared from *Bacillus brevis* S1 strain, which is a methanol-assimilating bacterium belonging to the genus *Bacillus*, in the same manner as described above. This chromosomal DNA was used as a template in PCR to amplify the target DNA region. The sequences of oligonucleotides for PCR (SEQ ID NOS: 12 and 13) were designed so that HindIII restriction enzyme sites should be introduced at the both ends of the amplified DNA fragment. The PCR conditions were the same as those used above. Then, the obtained DNA fragment was purified in a conventional manner and then treated with a restriction enzyme HindIII to prepare the target DNA having HindIII-digested ends at the both ends.

Separately, pHY300PLK was treated with a restriction enzyme HindIII, then treated with an alkaline phosphatase and ligated with the aforementioned DNA fragment by using T4 ligase (Takara Shuzo). This was used to transform the *E. coli* JM109 strain in the same manner as described above to obtain many tetracycline resistant colonies. Several colonies were selected from them, and plasmids contained in them were investigated to select one in which the target genes, the hps gene and phi gene, existed in the same direction as that of the tetracycline resistance gene on the vector. This plasmid was designated as pHY-H4.

Then, the AM101 strain mentioned in Example 1 was transformed in a conventional manner with each of pHY-H4 constructed as described above and pHY300PLK, which was the vector used for the construction of pHY-H4, respectively, to obtain transformants, pHY-H4/AM101 strain and pHY300PLK/AM101 strain. Colonies of each strain were picked up, inoculated into 5 ml of LB medium containing 10 μg/ml of tetracycline and 5 μg/ml of chloramphenicol and then cultured at 30° C. for 16 hours. Then, 0.1 ml of the culture broth was transferred into 5 ml of fresh LB medium containing the same antibiotics as mentioned above and further cultured at 37° C. for 8 hours. The culture broth was centrifuged (10,000 g, 10 minutes) to collect the cells.

The obtained cells are suspended in 0.9 ml of suspension buffer (Composition per 10 ml: 5 ml of 0.1 M potassium phosphate buffer (pH 7.6), 0.3 ml of 0.1 M magnesium chloride and 50 μl of 0.2 M dithiothreitol, filled up to 10 ml with sterilized water), subjected to ultrasonication while maintaining the temperature at 4° C. and centrifuged at 4° C. (at 20000 g for 10 minutes), and the supernatant portion was collected to prepare a cell extract. Then, the HPS activity and PHI activity present in each extract were investigated as described below.

In a volume of 0.9 ml of reaction buffer (composition is shown below) was incubated in a quartz cuvette at 47° C. for 3 minutes. Then, 50 μl of the cell extract prepared as described above was added to the reaction buffer and stirred sufficiently. At the same time, there was started time course measurement of absorbance of the reaction mixture at 340 nm, at which NADPH shows the absorption maximum. Sixty seconds after the addition of the cell extract, 50 μl of 1 M formaldehyde aqueous solution was added to the reaction mixture and stirred sufficiently. Then, increase of absorbance of the reaction mixture at 340 nm, i.e., generation of NADPH, was recorded. While increase of absorbance at 340 nm due to the addition of formaldehyde was not substantially observed for the case of using the extract from the control strain, the AM101 strain harboring pHY300PLK, rapid increase of the absorbance was observed for the case of using the strain harboring pHY-H4. This indicated that the products of the hps gene and phi gene cloned on pHY-H4 each expressed enzymatic activity in the *Bacillus subtilis* to finally produce fructose 6-phosphate from formaldehyde and ribulose 5-phosphate. Thus, it was confirmed that the hps gene and the phi gene had been cloned.

TABLE 1

| Composition of reaction buffer | |
|---|---|
| 0.1 M Potassium phosphate buffer (pH 7.6) | 5 ml |
| 0.1 M Magnesium chloride | 0.5 ml |
| 0.1 M Ribose 5-phosphate | 0.5 ml |
| 10 mM NADP | 2.5 ml |
| Phosphoriboisomerase | 30 μl |
| Phosphoglucoisomerase | 20 μl |
| Glucose 6-phosphate dehydrogenase | 20 μl |
| Sterilized water | 0.5 ml |
| Total | 9.07 ml |

Example 5

Construction of Plasmid Containing hps, phi and amd

The plasmids pHY-A2 and pHY-H4 produced in Examples 3 and 4 were each treated with two kinds of restriction enzymes, Bgl II and EcoT22I. From pHY-A2, a smaller DNA fragment containing the amd gene was prepared. On the other hand, from pHY-H4, a larger DNA fragment containing the hps and phi genes was prepared in a conventional manner and ligated to the amd gene fragment by using T4 ligase.

Competent cells of *E. coli* JM109 strain were transformed by using the above reaction mixture. Transformants were selected by using tetracycline resistance as an index. From several tens of colonies emerged on an agar plate, 6 colonies were arbitrarily selected, and structures of plasmids contained in them were analyzed. As a result, it was confirmed that all the plasmids had the intended structure, i.e., a structure in which the three kinds of genes, amd, hps, and phi, were carried on the vector of pHY300PLK. This plasmid was designated as pHY-A2H4.

Example 6

**Preparation of *Bacillus subtilis* Strain Imparted with Methanol Utilization Ability and Assay of Methanol Utilization Ability of the Same**

The L-217M1 strain constructed in Example 2 was cultured overnight at 30° C. in LB liquid medium containing 5 μg/ml of chloramphenicol with shaking. In a volume of 0.1 ml of the culture broth was added to 5 ml of CI medium (composition is shown below) containing 5 μg/ml of chloramphenicol and stirred, and the cells were cultured at 37° C. with shaking. Absorbance of the culture broth was measured (660 nm) with an appropriate interval, and 60 minutes after the absorbance exceeded 1, the culture broth was centrifuged (3,000 g, 10 minutes) to collect the cells.

Then, the collected cells were suspended in 10 ml of CII medium (containing 5 μg/ml of chloramphenicol, composition is shown below) and further cultured for 40 minutes in this culture broth comprising CII medium with shaking. Then, 500 μl of the culture broth was extracted and added with 1 μg of pHY-A2H4, and the cells were cultured at 37° C. for 90 minutes with shaking. This culture broth was diluted appropriately and then inoculated on LB agar medium containing 5 μg/ml of chloramphenicol and 10 μg/ml of tetracycline, and the cells were cultured overnight at 37° C. as standing culture to select colonies exhibiting resistance to the both antibiotics. One of them was pHY-A2H4/L-217M1 strain.

The pHY-A2H4/L-217M1 strain was designated as AJ13855, and deposited at the independent administrative institution, National Institute of Advanced Industrial Science and Technology, International Patent Organism Depository (postal code 305-5466, Chuo Dai-6, 1-1 Higashi 1-Chome, Tsukuba-shi, Ibaraki-ken, Japan) on Aug. 2, 2001 and given with an accession number of FERM P-18447. Then, the deposition was changed to an international deposition under the provisions of the Budapest Treaty on Aug. 19, 2002 and given with an accession number of FERM BP-8154.

In a volume of 5 ml of CI medium was prepared as follows. First, 2.5 ml of 2× Solution A ($K_2HPO_4$: 2.8%, $KH_2PO_4$: 1.2%, $(NH_4)_2SO_4$: 0.4%) was added with 5 μl of a trace amount element solution ($CaCl_2$: 0.55 g, $ZnCl_2$: 0.17 g, $CuCl_2.2H_2O$: 0.043 g, $CoCl_2.6H_2O$: 0.06 g, $Na_2MoO_4.2H_2O$: 0.06 g per 100 ml), 1 μl of $FeCl_3$ solution and 1 μl of $MnSO_4$ solution, mixed and then added with 2.5 ml of 2× Solution B ($MgSO_4.7H_2O$: 10 mM, glucose: 1%), 50 μl of 5% (w/v) yeast extract, 10 μl of 10% (w/v) casamino acid, 50 μl of 5 mg/ml L-tryptophan solution, 50 μl of 5 mg/ml L-methionine solution and 50 μl of 2.5 mg/ml thymine solution. $K_2HPO_4$ and $KH_2PO_4$ can be purchased from Nakarai Tesque, $(NH_4)_2SO_4$, $MgSO_4.7H_2O$ and glucose can be purchased from Junsei Chemical, and yeast extract and casamino acid can be purchased from DIFCO. $CaCl_2$, $ZnCl_2$, $CuCl_2.2H_2O$, $CoCl_2.6H_2O$ and $Na_2MoO_4.2H_2O$ can be purchased from Wako Pure Chemical Industries.

In a volume of 10 ml of CII medium was prepared as follows. First, 5 ml 2× Solution A was added with 10 μl of the trace amount element solution, 2 μl of the $FeCl_3$ solution and 2 μl of the $MnSO_4$ solution and mixed. Then, this solution was added with 5 μl of 2× Solution B, 10 μl of 5% (w/v) yeast extract, 10 μl of 10% (w/v) casamino acid, 10 μl of 5 mg/ml L-tryptophan solution, 10 μl of 5 mg/ml L-methionine solution and 10 μl of 2.5 mg/ml thymine solution.

Then, by using methanol labeled with a stable isotope $^{13}C$, it was examined whether the constructed AJ13855 (pHY-A2H4/L-217M1) strain could utilize methanol. The AJ13855 strain was cultured overnight at 30° C. in LB liquid medium containing 5 μg/ml of chloramphenicol and 10 μg/ml of tetracycline with shaking. This culture broth was inoculated into LB liquid medium containing 5 μg/ml of chloramphenicol and 10 μg/ml of tetracycline at a ratio of 1% (v/v), culture was performed at 37° C. for 6 hours with shaking, and the culture broth was inoculated each of the following media, i.e., Medium A containing $^{13}C$-labeled methanol and Medium A containing ordinary methanol, at a ratio of 3% (v/v).

Composition of Medium A was indicated in Table 2. A medium obtained by adding $^{13}C$-labeled methanol to 50 ml of Medium A at a final concentration of 0.4% (v/v) of final concentration and a medium obtained by adding non-$^{13}C$-labeled ordinary methanol to 50 ml of Medium A at a final concentration of 0.4% (v/v) were used. After inoculation, the cells were cultured at 47° C. for 30 hours with shaking. After the culture, absorbance at 660 nm of the both culture broths, which indicated degree of growth, reached about 2.3, and thus there was no significant difference in growth of the bacterium between the both media. Then, the both culture broths were centrifuged (at 8000 rpm for 15 minutes) to obtain supernatants, and they were lyophilized.

In an amount of 62 mg of the lyophilized powder obtained from each of the culture broths was dissolved in 500 μl of heavy water. When amount of L-lysine in both of the solutions was measured, it was about 0.55 mg in the both solutions, and thus it was found that the amounts of L-lysine in the both solutions were almost the same. Then, the solutions were analyzed by $^{13}C$-NMR (nuclear magnetic resonance analysis apparatus) to investigate the ratio of $^{13}C$ in the produced L-lysine molecules. As a result, compared with the signal for the carbon atoms of L-lysine produced by the culture using addition of the non-labeled methanol, an about 3.8 to 13 times stronger signal were detected for L-lysine produced by the culture using addition of the $^{13}C$-labeled methanol. This indicated that the constructed AJ13855 (pHY-A2H4/L-217M1) strain newly acquired an ability to take up the $^{13}C$-labeled methanol added to the medium and even utilize it for the production of L-lysine.

TABLE 2

| Composition of Medium A (per 130 ml) | |
|---|---|
| 5 × MM Medium (composition is shown below) | 26 ml |
| 50 mM $MgSO_4$ | 2.6 ml |
| Trace amount element solution | 1.3 ml |
| 2 mg/ml $FeSO_4$ | 260 μl |
| 0.1 mg/ml $MnSO_4$ | 260 μl |
| 5 mg/ml L-Tryptophan | 1.3 ml |
| 5 mg/ml L-Methionine | 1.3 ml |
| 2.5 mg/ml Thymine | 1.3 ml |
| 50% (w/v) Glucose | 1.3 ml |
| 50% (w/v) Ribose | 1.3 ml |
| 10 mg/ml (w/v) Tetracycline | 65 μl |
| Sterilized water | 93 ml |
| 5 × MM medium (per 200 ml) | |
| $(NH_4)_2SO_4$ | 2 g |
| $K_2HPO_4$ | 14 g |
| $KH_2PO_4$ | 6 g |
| Sodium citrate dihydrate | 1 g |
| $MgSO_4.7H_2O$ | 0.2 g |

Filled up to a total volume of 200 ml with sterilized water

What is claimed is:

1. A method for producing an L-amino acid in a bacterium comprising
   a) culturing the bacterium in a medium that contains methanol as a carbon source.
   b) producing and accumulating the L-amino acid in the medium or within cells of the bacterium, and
   c) collecting the L-amino acid from the medium or the cells of the bacterium, using a bacterium that has:
      i) a methanol dehydrogenase gene introduced to impart or enhance an ability to utilize methanol as compared to a wild-type bacterium, and
      ii) been modified so that activities of hexulose phosphate synthase and phosphohexuloisomerase are enhanced as compared to a wild-type bacterium by:
         increasing the copy number of the genes coding for hexulose phosphate synthase and phosphohexuloisomerase,
         replacing expression regulatory sequences of the genes coding for hexulose phosphate synthase and phosphohexuloisomerase with stronger expression regulatory sequences
         or a combination of modifications thereof.

2. The method according to claim 1, wherein the bacterium is a bacterium to which a gene coding for a methanol dehydrogenase activator is further introduced.

3. The method according to claim 2, wherein the L-amino acid is L-lysine.

4. The method according to claim 2, wherein the bacterium is a bacterium belonging to the genus *Bacillus*.

5. The method according to claim 1, wherein the L-amino acid is L-lysine.

6. The method according to claim 1, wherein the bacterium is a bacterium belonging to the genus *Bacillus*.

7. The method according to claim 1, wherein the gene coding for hexulose phosphate synthase comprises nucleotides 508 to 1140 of SEQ ID NO: 16 and wherein the gene coding for phosphohexuloisomerase comprises nucleotides 1149 to 170 of SEQ ID NO: 16.

8. The method according to claim 1, wherein the gene coding for methanol dehydrogenase comprises GenBank Accession No. M65004.

9. A bacterium to which a methanol dehydrogenase gene is introduced, wherein the microorganism is modified so that hexulose phosphate synthase and phosphohexuloisomerase are enhanced by increasing the copy number of the genes coding for hexulose phosphate synthase and phosphohexuloisomerase, substituting expression regulatory sequences of genes with stronger expression regulatory sequences or a combination thereof and an ability to utilize methanol is imparted or enhanced.

10. The bacterium according to claim 9, to which a gene coding for a methanol dehydrogenase activator is further introduced.

11. The bacterium according to claim 10, which is a Gram positive bacterium.

12. The bacterium according to claim 11, which is a bacterium belonging to the genus *Bacillus*.

13. The bacterium according to claim 11, which is *Bacillus subtilis*.

14. The bacterium according to claim 9, which is a Gram positive bacterium.

15. The bacterium according to claim 14, which is a bacterium belonging to the genus *Bacillus*.

16. The bacterium according to claim 15, which is *Bacillus subtilis*.

17. The bacterium according to claim 9, wherein the gene coding for hexulose phosphate synthase comprises nucleotides 508 to 1140 of SEQ ID NO: 16 and wherein the gene coding for phosphohexuloisomerase comprises the nucleotide sequence of nucleotides 1149 to 170 of SEQ ID NO: 16.

18. The bacterium according to claim 17, wherein the gene coding for methanol dehydrogenase comprises GenBank Accession No. M65004.

* * * * *

UNITED STATES PATENT AND TRADEMARK OFFICE
CERTIFICATE OF CORRECTION

PATENT NO. : 7,163,810 B2 Page 1 of 1
APPLICATION NO. : 10/234329
DATED : January 16, 2007
INVENTOR(S) : Hisashi Yasueda et al.

It is certified that error appears in the above-identified patent and that said Letters Patent is hereby corrected as shown below:

Column 37, Claim 1, line 28, " to a wild-type bacterium, and "
    should read -- to the corresponding wild-type bacterium, and --;
        line 31, " compared to a wild-type bacterium by: "
    should read -- compared to the corresponding wild-type bacterium by: --;
        Claim 7, line 55, "1149 to 170 of SEQ ID NO: 16. "
    should read -- 1149 to 1700 of SEQ ID NO: 16. --.

Column 38, Claim 17, line 49, " 1149 to 170 of SEQ ID NO: "
    should read -- 1149 to 1700 of SEQ ID NO: --.

Signed and Sealed this

Fifteenth Day of May, 2007

JON W. DUDAS
*Director of the United States Patent and Trademark Office*

SEQUENCE LISTING

<160> NUMBER OF SEQ ID NOS: 18

<210> SEQ ID NO 1
<211> LENGTH: 34
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
taaaaaggat ccccgatgat acaacaccaa acgg                                  34

<210> SEQ ID NO 2
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
gaccgaattc catgtagttt ttcctcattc acc                                   33

<210> SEQ ID NO 3
<211> LENGTH: 10186
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
aattcttgaa gacgaaaggg cctcgtgata cgcctatttt tataggttaa tgtcatgata      60
ataatggttt cttagacgtc aggtggcact tttcggggaa atgtgcgcgg aacccctatt     120
tgtttatttt tctaaataca ttcaaatatg tatccgctca tgagacaata accctgataa     180
atgcttcaat aatattgaaa aaggaagagt atgagtattc aacatttccg tgtcgccctt     240
attccctttt ttgcggcatt ttgccttcct gtttttgctc acccagaaac gctggtgaaa     300
gtaaaagatg ctgaagatca gttgggtgca cgagtgggtt acatcgaact ggatctcaac     360
agcggtaaga tccttgagag ttttcgcccc gaagaacgtt ttccaatgat gagcactttt     420
aaagttctgc tatgtggcgc ggtattatcc cgtgttgacg ccgggcaaga gcaactcggt     480
cgccgcatac actattctca gaatgacttg gttgagtact caccagtcac agaaaagcat     540
cttacggatg gcatgacagt aagagaatta tgcagtgctg ccataaccat gagtgataac     600
actgcggcca acttacttct gacaacgatc ggaggaccga aggagctaac cgcttttttg     660
cacaacatgg gggatcatgt aactcgcctt gatcgttggg aaccggagct gaatgaagcc     720
ataccaaacg acgagcgtga caccacgatg cctgcagcaa tggcaacaac gttgcgcaaa     780
ctattaactg gcgaactact tactctagct tcccggcaac aattaataga ctggatggag     840
gcggataaag ttgcaggacc acttctgcgc tcggcccttc cggctggctg gtttattgct     900
gataaatctg gagccggtga gcgtgggtct cgcggtatca ttgcagcact ggggccagat     960
ggtaagccct cccgtatcgt agttatctac acgacgggga gtcaggcaac tatggatgaa    1020
cgaaatagac agatcgctga gataggtgcc tcactgatta agcattggta actgtcagac    1080
caagtttact catatatact ttagattgat ttaaaacttc atttttaatt taaaaggatc    1140
taggtgaaga tcctttttga taatctcatg accaaaatcc cttaacgtga gttttcgttc    1200
cactgagcgt cagaccccgt agaaaagatc aaaggatctt cttgagatcc ttttttttctg    1260

-continued

```
cgcgtaatct gctgcttgca acaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agcattgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttttgtga   1800 tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcctga tgcggtattt tctccttacg    2040
catctgtgcg gtatttcaca ccgcatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagctg cggtaaagct catcagcgtg gtcgtgaagc gattcacaga    2340
tgtctgcctg ttcatccgcg tccagctcgt tgagtttctc cagaagcgtt aatgtctggc    2400
ttctgataaa gcgggccatg ttaagggcgg ttttttcctg tttggtcact tgatgcctcc    2460
gtgtaagggg gaatttctgt tcatgggggt aatgataccg atgaaacgag agaggatgct    2520
cacgatacgg gttactgatg atgaacatgc ccggttactg gaacgttgtg agggtaaaca    2580
actggcggta tggatgcggc gggaccagag aaaaatcact cagggtcaat gccagcgctt    2640
cgttaataca gatgtaggtg ttccacaggg tagccagcag catcctgcga tgcagatccg    2700
gaacataatg gtgcagggcg ctgacttccg cgtttccaga ctttacgaaa cacggaaacc    2760
gaagaccatt catgttgttg ctcaggtcgc agacgttttg cagcagcagt cgcttcacgt    2820
tcgctcgcgt atcggtgatt cattctgcta accagtaagg caaccccgcc agcctagccg    2880
ggtcctcaac gacaggagca cgatcatgcg cacccgtggc caggacccaa cgctgcccga    2940
gatgcgccgc gtgcggctgc tggagatggc ggacgcgatg gatatgttct gccaagggtt    3000
ggtttgcgca ttcacagttc tccgcaagaa ttgattggct ccaattcttg gagtggtgaa    3060
tccgttagcg aggtgccgcc ggcttccatt caggtcgagg tggcccggct ccatgcaccg    3120
cgacgcaacg cggggaggca gacaaggtat agggcggcgc ctacaatcca tgccaacccg    3180
ttccatgtgc tcgccgaggc ggcataaatc gccgtgacga tcagcggtcc agtgatcgaa    3240
gttaggctgg taagagccgc gagcgatcct tgaagctgtc cctgatggtc gtcatctacc    3300
tgcctggaca gcatggcctg caacgcgggc atcccgatgc cgccggaagc gagaagaatc    3360
ataatgggga aggccatcca gcctcgcgtc gcgactaaga aaatgccgtc aaatccgctc    3420
gccatgactt cactaacgat gcctttgaaa atcttcaagt tcttttctac taattcaagg    3480
cgtgtctcac caggtttttg gtttgctccg gcgcaaatgc agacaatatc agcatccttg    3540
cagggtatgt ttctctttga tgtcttttttg tttgtgaagt atttcacatt tatattgtgc    3600
```

```
aacacttcac aaacttttgc aagagaaaag ttttgtctga tttatgaaca aaaagaaac    3660
catcattgat ggtttctttc ggtaagtccc gtctagcctt gccctcaatg gggaagagaa    3720
ccgcttaagc ccgagtcatt atataaacca tttagcacgt aatcaaagcc aggctgattc    3780
tgaccgggca cttgggcgct gccattatta aaaatcactt ttgcgttggt tgtatccgtg    3840
tccgcaggca gcgtcagcgt gtaaattccg tctgcatttt tagtcattgg ttttccaggc    3900
caagatccgg tcaattcaat tactcggctc ccatcatgtt tatagatata agcatttacc    3960
tggctccaat gattcggatt ttgatagccg atggttttgg ccgacgctgg atctctttta    4020
acaaaactgt atttctcggt cctcgttaca ccatcactgt tcgttccttt taacatgatg    4080
gtgtatgttt tgccaaattg gatctccttt tccgattgtg aattgatctc catccttaaa    4140
cgcctgtcgt ctggtccatt attgatttga taaacggctt ttgttgtatt cgcatctgca    4200
cgcaaggtaa tcgtcagttg atcattgaaa gaatgtgtta cacctgtttt gtaattctca    4260
aggaaaacat gaggcgcttt tgcaatatca tcaggataaa gcacagctac agacctggca    4320
ttgatcgtgc ctgtcagttt accatcgttc acttgaaatg aacccgctcc agctttattg    4380
tcatacctgc catcaggcaa ttttgttgcc gtattgatag agacagagga tgaacctgca    4440
tttgccagca caacgccatg tgagccgcgc tgattcataa atatctggtt gtttccattc    4500
gggttcgaga gttcctcagg ctgtccagcc atcacattgt gaaatctatt gaccgcagtg    4560
atagcctgat cttcaaataa agcactcccg cgatcgccta tttggctttt ccccgggaac    4620
ctcacaccat ttccgcctcc ctcaggtctg gaaaagaaaa gaggcgtact gcctgaacga    4680
gaagctatca ccgcccagcc taaacggata tcatcatcgc tcatccatgt cgacgctctc    4740
ccttatgcga ctcctgcatt aggaagcagc ccagtagtag gttgaggccg ttgagcaccg    4800
ccgccgcaag gaatggtgca tgcaaggaga tggcgcccaa cagtcccccg gccacggggc    4860
ctgccaccat acccacgccg aaacaagcgc tcatgagccc gaagtggcga gcccgatctt    4920
ccccatcggt gatgtcggcg atataggcgc cagcaaccgc acctgtggcg ccggtgatgc    4980
cggccacgat gcgtccggcg tagaggatct ggagctgtaa tataaaaacc ttcttcaact    5040
aacgggcag gttagtgaca ttagaaaacc gactgtaaaa agtacagtcg gcattatctc    5100
atattataaa agccagtcat taggcctatc tgacaattcc tgaatagagt tcataaacaa    5160
tcctgcatga taaccatcac aaacagaatg atgtacctgt aaagatagcg gtaaatatat    5220
tgaattacct ttattaatga attttcctgc tgtaataatg ggtagaaggt aattactatt    5280
attattgata tttaagttaa acccagtaaa tgaagtccat ggaataatag aaagagaaaa    5340
agcatttca ggtataggtg ttttgggaaa caatttcccc gaaccattat atttctctac    5400
atcagaaagg tataaatcat aaaactcttt gaagtcattc tttacaggag tccaaatacc    5460
agagaatgtt ttagatacac catcaaaaat tgtataaagt ggctctaact tatcccaata    5520
acctaactct ccgtcgctat tgtaaccagt tctaaaagct gtatttgagt ttatcaccct    5580
tgtcactaag aaaataaatg cagggtaaaa tttatatcct tcttgttta tgtttcggta    5640
taaaacacta atatcaattt ctgtggttat actaaaagtc gtttgttggt tcaaataatg    5700
attaaatatc tcttttctct tccaattgtc taaatcaatt ttattaaagt tcatttgata    5760
tgcctcctaa attttatct aaagtgaatt taggaggctt acttgtctgc tttcttcatt    5820
agaatcaatc cttttttaaa gtcaatatta ctgtaacata aatatatatt ttaaaaatat    5880
cccactttat ccaattttcg tttgttgaac taatgggtgc tttagttgaa gaataaagac    5940
cacattaaaa aatgtggtct tttgtgtttt tttaaaggat ttgagcgtac gcgaaaaatc    6000
```

```
cttttctttc tttcttatct tgataataag ggtaactatt gccgatgata agctgtcaaa   6060
catgagaatt cccggggatc tgaatttgcc tggcggcagt agcgcggtgg tcccacctga   6120
ccccatgccg aactcagaag tgaaacgccg tagcgccgat ggtagtgtgg ggtctcccca   6180
tgcgagagta gggaactgcc aggcatcaaa taaaacgaaa ggctcagtcg aaagactggg   6240
cctttcgttt tatctgttgt ttgtcggtga acgctctcct gagtaggaca aatccgccgg   6300
gagcggattt gaacgttgcg aagcaacggc ccggagggtg cgggcagga cgcccgccat   6360
aaactgccag gcatcaaatt aagcagaagg ccatcctgac ggatggcctt tttgcgtttc   6420
tacaaactct ttttgtttat ttttctaaat acattcaaat atgtatccgc tcatgagaca   6480
ataaccctga taaatgcttc aataatcctg aagtcgggga tctctgcagt cgcgatgatt   6540
aattaattca gaacgctcgg ttgccgccgg gcgttttttta tgcagcaatg gcaagaacgt   6600
tgctctagaa taattctaca cagcccagtc cagactattc ggcactgaaa ttatgggtga   6660
agtggtcaag acctcactag gcaccttaaa aatagcgcac cctgaagaag atttatttga   6720
ggtagccctt gcctacctag cttccaagaa agatatccta acagcacaag agcggaaaga   6780
tgttttgttc tacatccaga acaacctctg ctaaaattcc tgaaaaattt tgcaaaaagt   6840
tgttgacttt atctacaagg tgtggcataa tgtgtggaat tgtgagcgga taacaattaa   6900
gcttaaggag gtgatctaga gtcgacctgc agggatcccc agcttgttga tacactaatg   6960
ctttttttata tagggaaaag gtggtgaact actgtggaag ttactgacgt aagattacgg   7020
gtcgaccggg aaaaccctgg cgttacccaa cttaatcgcc ttgcagcaca tccccctttc   7080
gccagctggc gtaatagcga agaggcccgc accgatcgcc cttcccaaca gttgcgcagc   7140
ctgaatggcg aatggcgctt tgcctggttt ccggcaccag aagcggtgcc ggaaagctgg   7200
ctggagtgcg atcttcctga ggccgatact gtcgtcgtcc cctcaaactg gcagatgcac   7260
ggttacgatg cgcccatcta caccaacgta acctatccca ttacggtcaa tccgccgttt   7320
gttcccacgg agaatccgac gggttgttac tcgctcacat ttaatgttga tgaaagctgg   7380
ctacaggaag gccagacgcg aattattttt gatggcgtta actcggcgtt tcatctgtgg   7440
tgcaacgggc gctgggtcgg ttacggccag acagtcgtt tgccgtctga atttgacctg   7500
agcgcatttt tacgcgccgg agaaaaccgc ctcgcggtga tggtgctgcg ttggagtgac   7560
ggcagttatc tggaagatca ggatatgtgg cggatgagcg gcattttccg tgacgtctcg   7620
ttgctgcata aaccgactac acaaatcagc gatttccatg ttgccactcg ctttaatgat   7680
gatttcagcc gcgctgtact ggaggctgaa gttcagatgt gcggcgagtt gcgtgactac   7740
ctacgggtaa cagtttcttt atggcagggt gaaacgcagg tcgccagcgg caccgcgcct   7800
ttcggcggtg aaattatcgt gagcgccggt cgctaccatt accagttggt ctggtgtcaa   7860
aaataataat aaccgggcag gccatgtctg cccgtatttc gcgtaaggaa atccattatg   7920
tactatttca agctaattcg gtggaaacga ggtcatcatt tccttccgaa aaacggttg   7980
catttaaatc ttacatatgt aatactttca aagactacat tgtaagatt tgatgtttga   8040
gtcggctgaa agatcgtacg taccaattat tgtttcgtga ttgttcaagc cataacactg   8100
tagggatagt ggaaagagtg cttgatctgg ttacgatcaa tcaaatattc aaacggaggg   8160
agacgatttg atgaaaccag taacgttata cgatgtcgca gagtatgccg gtgtctctta   8220
tcagaccgtt tcccgcgtgg tgaaccaggc cagccacgtt tctgcgaaaa cgcgggaaaa   8280
agtggaagcg gcgatggcgg agctgaatta cattcccaac cgcgtggcac aacaactggc   8340
```

```
gggcaaacag tcgttgctga ttggcgttgc cacctccagt ctggccctgc acgcgccgtc   8400
gcaaattgtc gcggcgatta aatctcgcgc cgatcaactg ggtgccagcg tggtggtgtc   8460
gatggtagaa cgaagcggcg tcgaagcctg taaagcggcg gtgcacaatc ttctcgcgca   8520
acgcgtcagt gggctgatca ttaactatcc gctggatgac caggatgcca ttgctgtgga   8580
agctgcctgc actaatgttc cggcgttatt tcttgatgtc tctgaccaga cacccatcaa   8640
cagtattatt ttctcccatg aagacggtac gcgactgggc gtggagcatc tggtcgcatt   8700
gggtcaccag caaatcgcgc tgttagcggg cccattaagt tctgtctcgg cgcgtctgcg   8760
tctggctggc tggcataaat atctcactcg caatcaaatt cagccgatag cggaacggga   8820
aggcgactgg agtgccatgt ccggttttca acaaaccatg caaatgctga atgagggcat   8880
cgttcccact gcgatgctgg ttgccaacga tcagatggcg ctgggcgcaa tgcgcgccat   8940
taccgagtcc gggctgcgcg ttggtgcgga tatctcggta gtgggatacg acgataccga   9000
agacagctca tgttatatcc cgccgtcaac caccatcaaa caggattttc gcctgctggg   9060
gcaaaccagc gtggaccgct tgctgcaact ctctcagggc caggcggtga agggcaatca   9120
gctgttgccc gtctcactgg tgaaaagaaa accaccctg gcgcccaata cgcaaaccgc   9180
ctctccccgc gcgttggccg attcattaat gcagctggca cgacaggttt cccgactgga   9240
aagcgggcag tgagcgcaac gcaattaatg tgagttaggc atcgcatcct gtctcgcgtc   9300
gtcggtgatg acggtgaaaa cctctgacac atgcagctcc cggagacggt cacagcttgt   9360
ctgtaagcgg atgccgggag cagacaagcc cgtcagggcg cgtcagcggg tgttggcggg   9420
tgtcggggcg cagccatgac cctgagcgcc ggtcgctacc attaccagtt ggtctggtgt   9480
caaaaataat aataaccggg caggccatgt ctgcccgtat ttcgcgtaag gaaatccatt   9540
atgtactatt tcgatcagac cagttttttaa tttgtgtgtt tccatgtgtc cagtttggaa   9600
tactcttaac ctcattggaa atcgcggcat aatcactggt ggtatgattg atgaccgcgt   9660
caacaatgac ctttatgcca tattcttcag cggctgcaca catttcttta aattcttgtt   9720
cagtacctaa gtaacggttg ccaatttgat acgatgtcgg ctgatacagc cagtaccagt   9780
tcgacatgct tttatctcct tgattccctt cctttacttg gttaatcgga gatgtctgaa   9840
tggctgtata tcctgcatca tgaatatcct tcatattgtg ttttaacgta ttgaacgacc   9900
aattccatgc atgaagaatg gttccgcttt tgatcgacgg tgctgtaagc tcattcgatt   9960
tgttcgccgt ttcagcactc gcagccgccg gtcctgccag aaccaaatga acagcaata   10020
aaaatccagc gaataacggc agtaaagagg ttttgaatcg ttttgcaaac attcttgaca   10080
ctccttattt gatttttga agacttactt cggagtcaaa atccctctt acttcattct   10140
tccgcttcct cctttcaaac cgatgtgaag actggagaat tttgtt         10186
```

<210> SEQ ID NO 4
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
ctggtgtcaa aaataataat aaccgggcag gc                                  32

<210> SEQ ID NO 5
<211> LENGTH: 30
<212> TYPE: DNA
<213> ORGANISM: ARTIFICIAL SEQUENCE

-continued

```
<220> FEATURE:
<223> OTHER INFORMATION: SYNTHETIC DNA

<400> SEQUENCE: 5
ccagtaccag ttcgacatgc ttttatctcc                              30

<210> SEQ ID NO 6
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
ttctgcttcg gtatgtgatt gtgaagctgg c                            31

<210> SEQ ID NO 7
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
cctcaaccta ctactgggct gcttcctaat g                            31

<210> SEQ ID NO 8
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
agcgcccaag tgcccggtca gaatcagcct                              30

<210> SEQ ID NO 9
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
cgcttccaat cacccgctct tttggcaggc                              30

<210> SEQ ID NO 10
<211> LENGTH: 37
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
gctttgtttt tttgaattcc aagagacata cagccga                      37

<210> SEQ ID NO 11
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 11 cactttttt tgcaggttga attccgtttc                               30
```

<210> SEQ ID NO 12
<211> LENGTH: 39
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
cttatggaaa gctttggatc attcatacct tttttttccc					39

<210> SEQ ID NO 13
<211> LENGTH: 39
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
cgcgttggaa gctttcccat atggtcgaca ctatataaa					39

<210> SEQ ID NO 14
<211> LENGTH: 555
<212> TYPE: DNA
<213> ORGANISM: Bacillus subtilis
<220> FEATURE:
<221> NAME/KEY: CDS
<222> LOCATION: (1)..(555)
<223> OTHER INFORMATION:

<400> SEQUENCE: 14

| atg | aaa | tca | tta | gaa | gaa | aaa | aca | att | gcc | aaa | gaa | cag | att | ttt | tcg | 48 |
| Met | Lys | Ser | Leu | Glu | Glu | Lys | Thr | Ile | Ala | Lys | Glu | Gln | Ile | Phe | Ser | |
| 1 | | | | 5 | | | | | 10 | | | | | 15 | | |

| ggt | aaa | gtc | att | gat | ctt | tat | gtc | gag | gat | gta | gag | ctg | cca | aac | ggc | 96 |
| Gly | Lys | Val | Ile | Asp | Leu | Tyr | Val | Glu | Asp | Val | Glu | Leu | Pro | Asn | Gly | |
| | | | 20 | | | | | 25 | | | | | 30 | | | |

| aaa | gcc | agt | aaa | cgt | gaa | att | gtg | aaa | cac | cct | gga | gct | gta | gcg | gta | 144 |
| Lys | Ala | Ser | Lys | Arg | Glu | Ile | Val | Lys | His | Pro | Gly | Ala | Val | Ala | Val | |
| | 35 | | | | | 40 | | | | | 45 | | | | | |

| aaa | gcc | agt | aaa | cgt | gaa | att | gtg | aaa | cac | cct | gga | gct | gta | gcg | gta | 192 |
| Lys | Ala | Ser | Lys | Arg | Glu | Ile | Val | Lys | His | Pro | Gly | Ala | Val | Ala | Val | |
| 50 | | | | | 55 | | | | | 60 | | | | | | |

| aag | ccg | ctt | gag | cgg | acg | atc | gtt | gaa | att | ccg | gcc | ggt | aag | ctt | gaa | 240 |
| Lys | Pro | Leu | Glu | Arg | Thr | Ile | Val | Glu | Ile | Pro | Ala | Gly | Lys | Leu | Glu | |
| 65 | | | | 70 | | | | | 75 | | | | | 80 | | |

| aaa | ggt | gag | gag | ccg | gag | tat | acg | gca | ctt | cgg | gaa | ctt | gaa | gag | gaa | 288 |
| Lys | Gly | Glu | Glu | Pro | Glu | Tyr | Thr | Ala | Leu | Arg | Glu | Leu | Glu | Glu | Glu | |
| | | | | 85 | | | | | 90 | | | | | 95 | | |

| acc | ggt | tat | aca | gca | aaa | aaa | ctg | aca | aaa | ata | act | gcg | ttt | tat | aca | 336 |
| Thr | Gly | Tyr | Thr | Ala | Lys | Lys | Leu | Thr | Lys | Ile | Thr | Ala | Phe | Tyr | Thr | |
| | | | 100 | | | | | 105 | | | | | 110 | | | |

| tca | ccc | gga | ttt | gca | gat | gaa | atc | gtt | cac | gtt | ttt | ctt | gct | gag | gag | 384 |
| Ser | Pro | Gly | Phe | Ala | Asp | Glu | Ile | Val | His | Val | Phe | Leu | Ala | Glu | Glu | |
| | | 115 | | | | | 120 | | | | | 125 | | | | |

| ctt | tct | gtg | ctt | gaa | gaa | aaa | cgg | gag | ctt | gat | gag | gac | gag | ttt | gtt | 432 |
| Leu | Ser | Val | Leu | Glu | Glu | Lys | Arg | Glu | Leu | Asp | Glu | Asp | Glu | Phe | Val | |
| | 130 | | | | | 135 | | | | | 140 | | | | | |

| gaa | gtg | atg | gag | gtg | acg | ctt | gaa | gat | gcg | cta | aag | ctg | gtt | gaa | tcg | 480 |
| Glu | Val | Met | Glu | Val | Thr | Leu | Glu | Asp | Ala | Leu | Lys | Leu | Val | Glu | Ser | |
| 145 | | | | | 150 | | | | | 155 | | | | | 160 | |

| cgt | gaa | gta | tat | gat | gct | aaa | aca | gcc | tac | gcg | att | cag | tat | ctt | cag | 528 |
| Arg | Glu | Val | Tyr | Asp | Ala | Lys | Thr | Ala | Tyr | Ala | Ile | Gln | Tyr | Leu | Gln | |
| | | | | 165 | | | | | 170 | | | | | 175 | | |

```
        ctg aaa gaa gcg ctc caa gca caa aaa                                555
        Leu Lys Glu Ala Leu Gln Ala Gln Lys
                    180                 185

<210> SEQ ID NO 15
<211> LENGTH: 185
<212> TYPE: PRT
<213> ORGANISM: Bacillus subtilis

<400> SEQUENCE: 15

Met Lys Ser Leu Glu Glu Lys Thr Ile Ala Lys Glu Gln Ile Phe Ser
1               5                   10                  15

Gly Lys Val Ile Asp Leu Tyr Val Glu Asp Val Glu Leu Pro Asn Gly
            20                  25                  30

Lys Ala Ser Lys Arg Glu Ile Val Lys His Pro Gly Ala Val Ala Val
        35                  40                  45

Lys Ala Ser Lys Arg Glu Ile Val Lys His Pro Gly Ala Val Ala Val
    50                  55                  60

Lys Pro Leu Glu Arg Thr Ile Val Glu Ile Pro Ala Gly Lys Leu Glu
65                  70                  75                  80

Lys Gly Glu Glu Pro Glu Tyr Thr Ala Leu Arg Glu Leu Glu Glu Glu
                85                  90                  95

Thr Gly Tyr Thr Ala Lys Lys Leu Thr Lys Ile Thr Ala Phe Tyr Thr
            100                 105                 110

Ser Pro Gly Phe Ala Asp Glu Ile Val His Val Phe Leu Ala Glu Glu
        115                 120                 125

Leu Ser Val Leu Glu Glu Lys Arg Glu Leu Asp Glu Asp Glu Phe Val
    130                 135                 140

Glu Val Met Glu Val Thr Leu Glu Asp Ala Leu Lys Leu Val Glu Ser
145                 150                 155                 160

Arg Glu Val Tyr Asp Ala Lys Thr Ala Tyr Ala Ile Gln Tyr Leu Gln
                165                 170                 175

Leu Lys Glu Ala Leu Gln Ala Gln Lys
            180                 185

<210> SEQ ID NO 16
<211> LENGTH: 1823
<212> TYPE: DNA
<213> ORGANISM: Bacillus brevis
<220> FEATURE:
<221> NAME/KEY: CDS
<222> LOCATION: (508)..(1140)
<223> OTHER INFORMATION:

<400> SEQUENCE: 16
agccaatgac ggaaaatgat tgaggcattt tttgatccag aaataaatta tacaaagcag      60
gatagatttt cctttagct aaatcccctg tcgcgccaaa caagacaaag gtcatcgaat      120
ccacttttca tacctccaca ttaacatttg ttgcggcaaa tattagtata atatgtatat     180
tttttatatg taagtacgca cttattaatc ttatagttac aaatttatat aaagtataaa     240
taatatacta taaaaaatct tatggaaagt gatggatcat tcataccttt ttttcccgta    300
ttgtttacat tttctatagg aattttttct taatagtata cttttatac tatgtgttaa     360 taaagtgcgt actttttaaa aaatttgata gatagtatat taacagtgta caggcaaaag    420
aaggaataca cacatttgct tgtacaaatac aagttacat aattgtaaca aaaaaaacta    480 aaaatttga aaggagtgt ataattt atg caa ctt caa tta gct cta gat ttg      534
```

```
                              Met Gln Leu Gln Leu Ala Leu Asp Leu
                                1               5 gta aac att gaa gaa gca aaa caa gta gta gct gag gtt cag gag tat    582
Val Asn Ile Glu Glu Ala Lys Gln Val Val Ala Glu Val Gln Glu Tyr
 10              15                  20                  25 gtc gat atc gta gaa atc ggt act ccg gtt att aaa att tgg ggt ctt    630
Val Asp Ile Val Glu Ile Gly Thr Pro Val Ile Lys Ile Trp Gly Leu
                 30                  35                  40 caa gct gta aaa gaa gtt aaa gac gca ttc cct cat tta caa gtt tta    678
Gln Ala Val Lys Glu Val Lys Asp Ala Phe Pro His Leu Gln Val Leu
             45                  50                  55 gct gac atg aaa act atg gat gct gca gca tat gaa gtt gct aaa gca    726
Ala Asp Met Lys Thr Met Asp Ala Ala Ala Tyr Glu Val Ala Lys Ala
         60                  65                  70 gct gag cat ggc gct gat atc gta aca att ctt gca gca gct gaa gat    774
Ala Glu His Gly Ala Asp Ile Val Thr Ile Leu Ala Ala Ala Glu Asp
     75                  80                  85 gta tca att aag ggt gct gta gaa gaa gcg aaa aaa ctt ggc aaa aaa    822
Val Ser Ile Lys Gly Ala Val Glu Glu Ala Lys Lys Leu Gly Lys Lys
 90              95                 100                 105 atc ctt gtt gac atg atc gca gtt aaa aat tta gaa gag cgt gca aaa    870
Ile Leu Val Asp Met Ile Ala Val Lys Asn Leu Glu Glu Arg Ala Lys
                110                 115                 120 caa gtg gat gaa atg ggt gta gac tac att tgt gtt cac gct gga tac    918
Gln Val Asp Glu Met Gly Val Asp Tyr Ile Cys Val His Ala Gly Tyr
            125                 130                 135 gat ctc caa gca gta ggt aaa aac cca tta gat gat ctt aag aga att    966
Asp Leu Gln Ala Val Gly Lys Asn Pro Leu Asp Asp Leu Lys Arg Ile
        140                 145                 150 aaa gct gtc gtg aaa aat gca aaa act gct att gca ggc gga atc aaa   1014
Lys Ala Val Val Lys Asn Ala Lys Thr Ala Ile Ala Gly Gly Ile Lys
    155                 160                 165 tta gaa aca ttg cct gaa gtt atc aaa gca gaa ccg gat ctt gtc att   1062
Leu Glu Thr Leu Pro Glu Val Ile Lys Ala Glu Pro Asp Leu Val Ile
170                 175                 180                 185 gtc ggc ggc ggt att gct aac caa act gat aaa aaa gca gca gct gaa   1110
Val Gly Gly Gly Ile Ala Asn Gln Thr Asp Lys Lys Ala Ala Ala Glu
                190                 195                 200 aaa ata aat aaa tta gtt aaa caa ggg tta tgatcagcat gcagacaact     1160
Lys Ile Asn Lys Leu Val Lys Gln Gly Leu
            205                 210 gaattcttat ctgaaatcgt aaaagaatta agtaattcgg ttaaccaaat cgccgatgaa  1220
gaagcggaag cactggtaaa cggaattctt caatcaaaga agtatttgt tgccggtgca   1280 ggaagatccg gttttatggc aaaatccttt gcgatgcgca tgatgcacat gggaattgat  1340
gcctatgtcg ttggcgaaac cgtaactcct aactatgaaa agaagacat tttaattatt   1400 ggatccggct ctgagaaaac aaaaggtctc gtttccatgg ctcaaaaagc aaaaagcata  1460
ggtggaacca ttgcggctgt aacgattaat cctgaatcaa caatcggaca attagcggat  1520
atcgttatta aaatgccagg ttcgcctaaa gataaatcag aagcaaggga actattcaa   1580 ccaatgggat ccctttttcga gcaaacatta ttattattct atgatgctgt cattttgaga  1640
ttcatggaga aaaaggcttt ggatacaaaa acaatgtacg gaagacatgc caatctcgag  1700
taggcgtgga attaagaaaa ggaagaccgc gatgctttgc ggtctttcct tgttttttt   1760 acattacatg atgtttatat agtgtcgacc atatgggaga gctcccaacg cgttggatgc  1820
ata                                                                1823
```

```
<210> SEQ ID NO 17
<211> LENGTH: 211
<212> TYPE: PRT
<213> ORGANISM: Bacillus brevis

<400> SEQUENCE: 17

Met Gln Leu Gln Leu Ala Leu Asp Leu Val Asn Ile Glu Glu Ala Lys
1               5                   10                  15

Gln Val Val Ala Glu Val Gln Glu Tyr Val Asp Ile Val Glu Ile Gly
                20                  25                  30

Thr Pro Val Ile Lys Ile Trp Gly Leu Gln Ala Val Lys Glu Val Lys
            35                  40                  45

Asp Ala Phe Pro His Leu Gln Val Leu Ala Asp Met Lys Thr Met Asp
        50                  55                  60

Ala Ala Tyr Glu Val Ala Lys Ala Ala Glu His Gly Ala Asp Ile
65                  70                  75                  80

Val Thr Ile Leu Ala Ala Glu Asp Val Ser Ile Lys Gly Ala Val
                85                  90                  95

Glu Glu Ala Lys Lys Leu Gly Lys Lys Ile Leu Val Asp Met Ile Ala
                100                 105                 110

Val Lys Asn Leu Glu Glu Arg Ala Lys Gln Val Asp Glu Met Gly Val
            115                 120                 125

Asp Tyr Ile Cys Val His Ala Gly Tyr Asp Leu Gln Ala Val Gly Lys
        130                 135                 140

Asn Pro Leu Asp Asp Leu Lys Arg Ile Lys Ala Val Val Lys Asn Ala
145                 150                 155                 160

Lys Thr Ala Ile Ala Gly Gly Ile Lys Leu Glu Thr Leu Pro Glu Val
                165                 170                 175

Ile Lys Ala Glu Pro Asp Leu Val Ile Val Gly Gly Ile Ala Asn
            180                 185                 190

Gln Thr Asp Lys Lys Ala Ala Glu Lys Ile Asn Lys Leu Val Lys
        195                 200                 205

Gln Gly Leu
    210

<210> SEQ ID NO 18
<211> LENGTH: 184
<212> TYPE: PRT
<213> ORGANISM: Bacillus brevis

<400> SEQUENCE: 18

Met Gln Thr Thr Glu Phe Leu Ser Gln Ile Val Lys Gln Leu Ser Asn
1               5                   10                  15

Ser Val Asn Gln Ile Ala Asp Gln Gln Ala Gln Ala Leu Val Asn Gly
                20                  25                  30

Ile Leu Gln Ser Lys Lys Val Phe Val Ala Gly Ala Gly Arg Ser Gly
            35                  40                  45

Phe Met Ala Lys Ser Phe Ala Met Arg Met Met His Met Gly Ile Asp
        50                  55                  60

Ala Tyr Val Val Gly Glu Thr Val Thr Pro Asn Tyr Glu Lys Glu Asp
65                  70                  75                  80

Ile Leu Ile Ile Gly Ser Gly Ser Gly Glu Thr Lys Gly Leu Val Ser
                85                  90                  95

Met Ala Gln Lys Ala Lys Ser Ile Gly Gly Thr Ile Ala Ala Val Thr
                100                 105                 110
```

-continued

```
Ile Asn Pro Glu Ser Thr Ile Gly Gln Leu Ala Asp Ile Val Ile Lys
    115                 120                 125

Met Pro Gly Ser Pro Lys Asp Lys Ser Glu Ala Arg Glu Thr Ile Gln
    130                 135                 140

Pro Met Gly Ser Leu Phe Glu Gln Thr Leu Leu Leu Phe Tyr Asp Ala
145                 150                 155                 160

Val Ile Leu Arg Phe Met Glu Lys Lys Gly Leu Asp Thr Lys Thr Met
                165                 170                 175

Tyr Gly Arg His Ala Asn Leu Glu
            180
```